United States Patent
Yu et al.

(10) Patent No.: US 8,986,652 B2
(45) Date of Patent: Mar. 24, 2015

(54) METHOD OF PREPARING [$^{123}$I]IODOOCTYL FENBUFEN AMIDE AND APPLICATION THEREOF

(71) Applicant: National Tsing Hua University, Hsinchu (TW)

(72) Inventors: Chung-Shan Yu, Hsinchu (TW);
Ho-Lien Huang, Hsinchu (TW);
Chun-Nan Yeh, Hsinchu (TW);
Wei-Yuan Lee, Hsinchu (TW);
Kang-Wei Chang, Hsinchu (TW);
Ying-Cheng Huang, Hsinchu (TW);
Kun-Ju Lin, Hsinchu (TW);
Ching-Shiuann Yang, Hsinchu (TW);
Shu-Fan Tien, Hsinchu (TW);
Wen-Chin Su, Hsinchu (TW);
Jenn-Tzong Chen, Hsinchu (TW);
Wuu-Jyh Lin, Hsinchu (TW);
Shiou-Shiow Farn, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 8 days.

(21) Appl. No.: 13/757,018

(22) Filed: Feb. 1, 2013

(65) Prior Publication Data
US 2014/0079633 A1    Mar. 20, 2014

(30) Foreign Application Priority Data
Sep. 17, 2012  (TW) .............................. 101134033 A

(51) Int. Cl.
*A61K 51/04*    (2006.01)
*C07C 231/12*   (2006.01)
*C07C 231/02*   (2006.01)
*C07B 59/00*    (2006.01)

(52) U.S. Cl.
CPC ............... *A61K 51/04* (2013.01); *C07C 231/12* (2013.01); *C07C 231/02* (2013.01); *C07B 59/001* (2013.01)
USPC .......... 424/1.85; 424/1.11; 424/1.89; 424/9.6

(58) Field of Classification Search
USPC .............. 424/1.1, 1.85, 1.89, 9, 9.6; 564/169, 564/183, 184, 186
See application file for complete search history.

(56) References Cited

U.S. PATENT DOCUMENTS 5,609,848 A * 3/1997 Wilbur et al. ................. 424/1.85
7,736,624 B2 * 6/2010 Marnett et al. ................. 424/9.6

OTHER PUBLICATIONS

Kun-I Lin et al. Synthesis and Structure-Activity Relationship of Fenbufen Amide Analogs, Molecule, 2010, 15, 8796-8803.*

* cited by examiner

*Primary Examiner* — Michael G Hartley
*Assistant Examiner* — Jagadishwar Samala
(74) *Attorney, Agent, or Firm* — WPAT, P.C.; Anthony King; Kay Yang

(57) ABSTRACT

The present invention provides a method of preparing [$^{123}$I]Iodooctyl fenbufen amide with a radiochemical yield of 15%, a specific activity of 37 GBq/μmol and radiochemical purity of 95%. The present invention further provides a method of applying [$^{123}$I]Iodooctyl fenbufen amide as tracer of single photon emission computer tomography (SPECT) to estimate the distribution of cyclooxygenase. By the binding characteristics of the iodine isotope-labeled compounds and the positive correlation of inflammation to tumor lesion, the present invention can estimate the tumor development and metastasis.

3 Claims, 11 Drawing Sheets

METHOD OF PREPARING [$^{123}$I]IODOOCTYL FENBUFEN AMIDE AND APPLICATION THEREOF

CROSS-REFERENCE TO RELATED APPLICATIONS

This application claims the priority benefit of Taiwan application serial no. 101134033, filed on 17 Sep. 2012. The disclosure of the Taiwan application is incorporated by reference herein.

BACKGROUND OF THE INVENTION

1. Field of the Invention

The present invention relates to a method of preparing [$^{123}$I]Iodooctyl fenbufen amide and application.

2. The Prior Arts

Non steroid anti inflammatory drugs (NSAIDs) have been well recognized for their anti inflammatory efficacy. NSAIDs are including many types of drugs, such as aspirin, naproxen, diclofenac sodium, ibuprofen and fenbufen. Chronic inflammation is associated with an increased risk of cancer for individuals with inflammatory bowel diseases. Hence, cancer prevention by these NSAIDs is a perceivable concept.

The inflammatory mechanism is mainly associated with the inflammatory lipids which are catalyzed by a key enzyme, cyclooxygenase (COX). COX converts arachidonic acid (AA) to prostaglandin $H_2$ ($PGH_2$) via two sequential steps, and $PGH_2$ is the precursor of the series-2 prostanoids. Therefore, the cyclooxygenase plays a central role in a series of inflammatory signals. COX contains two active sites: a heme with peroxidase activity, responsible for the reduction of $PGG_2$ (Prostaglandins $G_2$) to $PGH_2$, and a cyclooxygenase site, where arachidonic acid is converted into the hydroperoxy endoperoxide prostaglandin $G_2$ ($PGG_2$). The reaction proceeds through H atom abstraction from arachidonic acid by a tyrosine radical generated by the peroxidase active site. Two $O_2$ molecules then react with the arachidonic acid radical, yielding $PGG_2$. Initial oxidation to $PGG_2$ by cyclooxygenase and subsequent reduction to an unstable endoperoxide intermediate $PGH_2$ by peroxidase. The two reactions displace in spatially distinct but mechanistically coupled active sites. The cyclooxygenase active site is located at the end of a long hydrophobic channel that is broad near the membrane-binding domain (the lobby) and narrows as it extends toward the interior of the protein. The peroxidase active site is located on the surface of the protein near the heme cofactor. In many tumors, higher prostaglandin levels are upregulated by COX.

Three types of COXs have been reported: COX-1, COX-2, and COX-3 in which (1) COX-1 is functioned as a housekeeping enzyme and constitutively expressed in most tissue types; (2) COX-2 is a highly inducible enzyme under physiological conditions; and (3) COX-3 is a splice mutation of COX-1, which retains intron one and has a frameshift mutation; thus some prefer the name COX-b or COX-1 variant (COX-1v). COX-1 is present in the most human tissue, such as gastric mucosa, kidney and platelet. COX-2 is mainly present in the macrophages and synovial cells, COX-2 causes inflammation reaction when the body hurt. NSAIDs can inhibit the activity of COX, and also block the formation of prostaglandin, prostacyclin and thromboxane to have pain-relieving effects and have the effect of reducing inflammation. Besides, the long-term uptake of NSAIDs has the effect of cancer prevention, but the uptake of non-specific anti-COX-1 inhibitors always accompanies with adverse side effects such as gastrointestinal toxicity. Therefore, specific anti COX-2 inhibitors were developed to overcome this side effect. However, prolonged use of COX-2 inhibitors encounters other side effects such as the cardiovascular events, it needs to limit the use. Due to the complexity of COX mechanism such as dual functionality of the enzyme and the close coupling of the two active sites, novel agents with unique inhibition is still under development.

Imaging of inflammation as well as tumor progression attracts a great attention recently. Being a diagnostic imaging probe for PET (Positron Emission Tomography) or SPECT (Single Photon Emission Computer Tomography) application, the cytotoxicity is not a serious concern since only very low dosage (lower than $\frac{1}{100}$ of the therapeutic dose) is administered by an individual within a short period. Various PET and SPECT tracers based on the structural characteristics of COX-2 and COX-1 specific inhibitors have been developed in the past decades. However, only rare radiopharmaceuticals have been successfully applied in imaging of inflammatory events. The probable cause has been attributed to the instability of COX-2 or due to the very low absolute amount of COX-2 overexpression for detection.

In present research, the radiolabeled [$^{18}$F]-N-(4-fluorobutyl)ethacrynic amide ([$^{18}$F]FBuEA) only shows the image of cold spot in rat liver tumor lesion, the physician or medical technologist can not observe the level of the radioactivity accumulated because only the image of hot spot can be observed the radiation intensity and the level of organ inflammation or lesion.

SUMMARY OF THE INVENTION

The present invention provides a method to prepare fenbufen derivatives, a member of NSAIDs, and also provides a method to use it as a tracer. Since design of these radiolabeled compounds of fenbufen derivatives were mainly based on the scaffold of the triphenyl ring or biaryl scaffolds with specific targeting to COX-1 and COX-2. Octyl fenbufen amide (OFA) was discovered through parallel solution phase synthesis derived library and the octyl group modified its antitumoral cytotoxicity in comparison with the parent fenbufen. Whereas, from antioxidant (e.g. NO) assay, the anti inflammatory effect of OFA was marginal. Thus, in the present invention, OFA was chosen for radiolabeling for imaging of COX-2 in vivo. Specifically, OFA was aimed to be labeled with radioiodine for noninvasive in-vivo imaging using SPECT.

The present invention provides Octyl fenbufen amide (OFA) derivatives with radioiodine labeling for SPECT to image inflammatory responses and tumor lesions. When investigating the structure of OFA, the proper position available for introducing radioiodine would be that carbon on the aromatic ring. [$^{123}$I]Iodooctyl fenbufen amide (the compound of formula 1) is prepared via dehalostannylation reaction of the radioiodine compound and organostannyl compound.

The present invention provides a method of preparing a compound of formula 1,

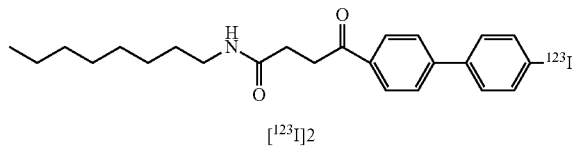

[$^{123}$I]2 comprising: (a) providing a compound of formula 3; and

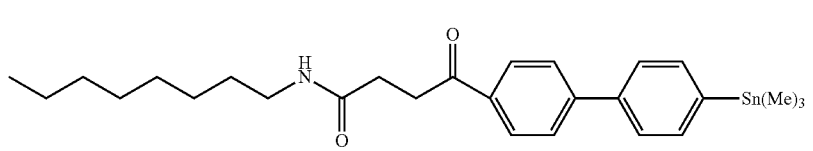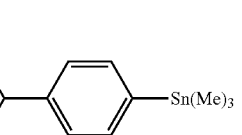

(b) reacting the compound of formula 3 with an $^{123}$I-labeled Iodine reagent and hydrogen peroxide to form the compound of formula 1, and the $^{123}$I-labeled Iodine reagent is $^{123}$I-labeled sodium iodide;

wherein the compound of formula 3 is formed by reacting a compound of formula 2

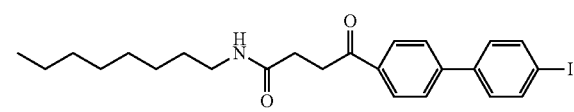

with bis(triphenylphosphine)palladium dichloride and a stannyl compound, wherein the stannyl compound is hexamethylditin ($Sn_2(CH_3)_6$).

In one embodiment, the compound of formula 2 is formed by reacting a compound of formula 4

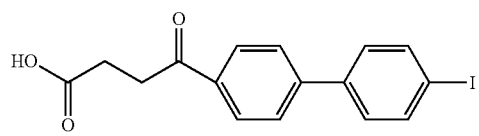

with O-benzotriazole-yl-N,N,N',N'-tetramethyl-uronium-hexafluoro-phosphate, diisopropyl ethylamine and 1-amino octane.

In another embodiment, the compound of formula 4 is formed by reacting a compound of formula 5

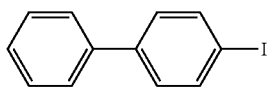

with succinic anhydride and $AlCl_3$.

The present invention provides a method of preparing the compound of formula 1 with a radiochemical yield of 15%, a specific activity of 37 GBq/μmol and radiochemical purity of 95%.

The present invention also provides a method of detecting the early inflammatory lesion of a tumor by using the compound of formula 1 as a tracer of an image-forming system, comprising combining the compound of formula 1 with cyclooxygenase to produce a signal, wherein the cyclooxygenase is cyclooxygenase-1 (COX-1) or cyclooxygenase-2 (COX-2), and the image-forming system is a single photon emission tomography (SPECT), the tumor is a liver tumor, the signal is a hot spot displayed by radioactive accumulation, and the hot spot is positively correlated to the tumor lesion.

The present invention provides a method of preparing the compound of formula 1 and a method of using the compound of formula 1 to estimate the distribution of cyclooxygenase. The present invention is applied in the single photon emission computer tomography (SPECT) image by the positive correlation of the distribution of cyclooxygenase to tumor lesion, and the present invention can estimate the tumor development and metastasis.

In present invention, further investigation of the binding affinity of the compound of formula 1 toward COX-1 and COX-2 using HPLC (High-performance liquid chromatography) in conjugation with a gel filtration column, the results indicate its preferential selectivity toward COX-2 rather than COX-1 with an affinity ratio of 1.4:1. In nonradioactive inhibition assay in vitro and small animal CT/SPECT image study, the distribution of radioactivity in the normal rat showed a homogeneous pattern, which was localized mainly in the liver in SPECT image. By contrast, SPECT images of the compound of formula 1 in a thioacetamide (TAA)-induced cholangiocarcionma (CCA) rat was displayed a higher uptake and heterogeneous pattern of radioactivity accumulation with hot spots in tumor lesions. The images in CCA rat indicate the positive correlation between hot spots and tumor lesions. The specimens of the liver of each of the two rats were further analyzed by histological stainings against COX-1 and COX-2. Clearly, the positive stainings of both COX-1 and COX-2 were solely found in the CCA tumor rat but not the normal rat. Hence, in the present invention, the compound of formula 1 could be a tracer of SPECT images to detect the inflammatory response and the tumor progression.

The detailed technology and above preferred embodiments implemented for the present invention are described in the following paragraphs accompanying the appended drawings for people skilled in this field to well appreciate the features of the claimed invention.

BRIEF DESCRIPTION OF THE DRAWINGS

FIG. 4 (B) is a SPECT/CT image of the CCA rat (feeding with TAA for 24 weeks) taken from 10 to 30 mins post injection. Injection dose: 0.76 mCi/1 mL. Lv: liver, H: heart, T: tumor.

Figure 1:
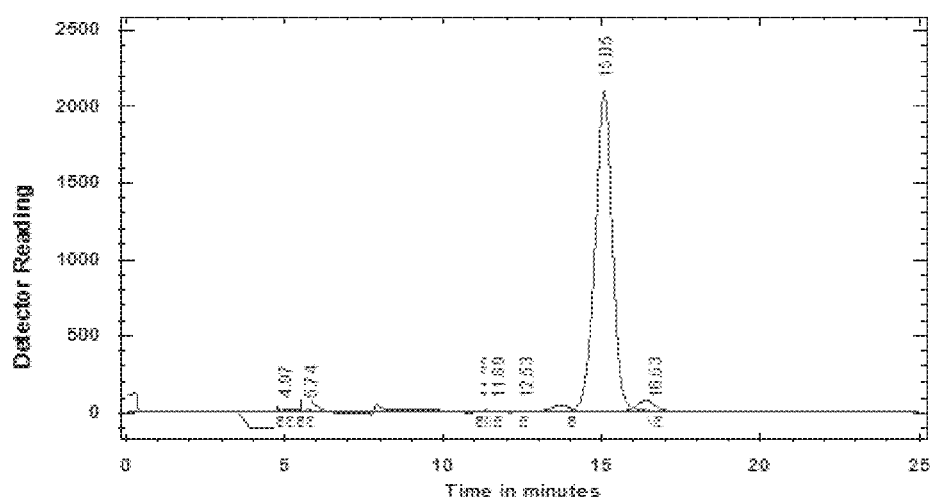
FIG. 1 is a chromatogram for the compound of formula 1 (15.05 min) by HPLC purification. Normal phase column (Si-100) was employed. Red line: radioactivity, blue line: UV signal at 254 nm.

DETAILED DESCRIPTION OF THE PREFERRED EMBODIMENT and toluene were dried over $CaH_2$ and MeOH was dried over Mg and distilled prior to reaction. DMF (N,N-dimethylformamide) and 1,4-dioxane were distilled under reduced pressure. Reagents and solvents were of reagent grade. Preparation of the compound of formula 3 was conducted in dried glasswares under a positive pressure of nitrogen. The eluents for flash chromatography such as EtOAc, acetone, and n-hexane were industrial grade and distilled prior to use; MeOH and $CHCl_3$ were reagent grade and used without further puri-

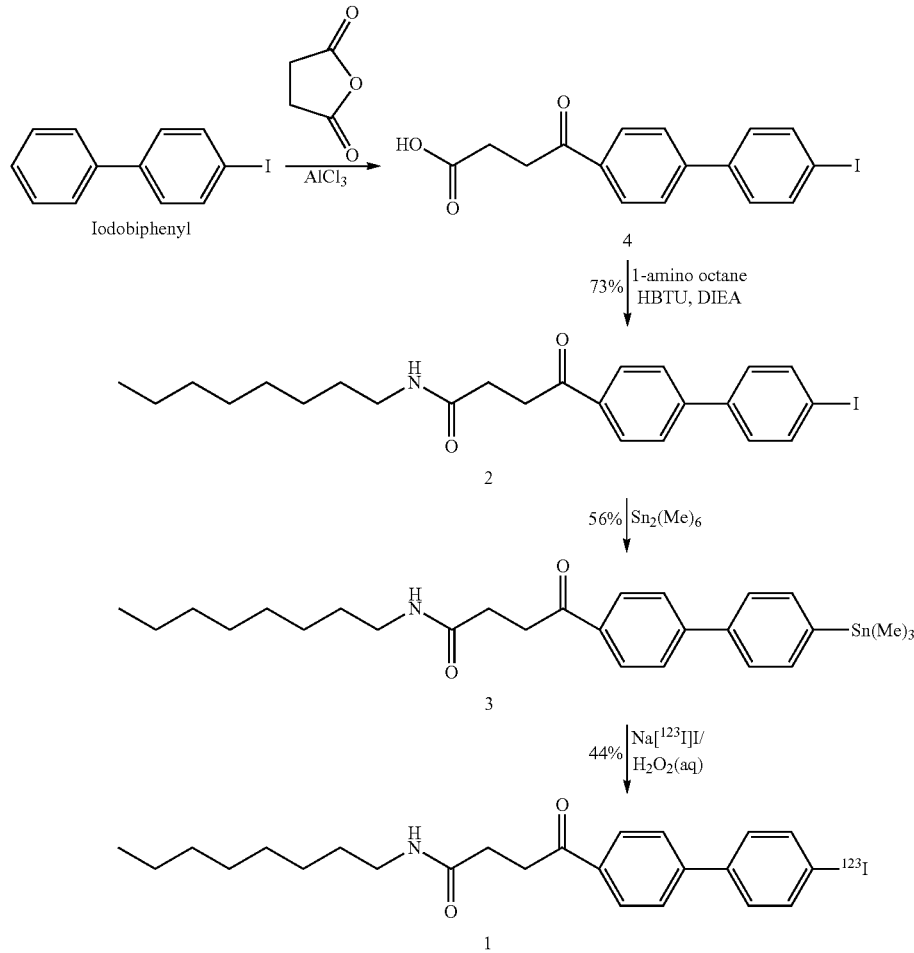

In Scheme I, the compound of formula 4 (4-(4'-iodobiphenyl-4-yl)-4-oxobutanoic acid) is formed by reacting 4-iodobiphenyl with succinic anhydride and $AlCl_3$, the compound of formula 2 (4-(4'-iodobiphenyl-4-yl)-N-octyl-4-oxobutanamide) is formed by reacting the compound of formula 4 with O-benzotriazol-1-yl-N,N,N',N'-tetramethyluronium hexafluorophosphoate (HBTU), diisopropyl ethylamine and 1-amino octane, the compound of formula 3 (N-octyl-4-oxo-4-(4'-(trimethylstannyl)biphenyl-4-yl) butanamide) is formed by reacting the compound of formula 2 with hexamethylditin, the compound of formula 1 (4-(4'-[$^{123}$I]iodobiphenyl-4-yl)-N-octyl-4-oxobutanamide) is formed by reacting the compound of formula 3 with [$^{123}$I]-labeled NaI and hydrogen peroxide.

General Preparation

All reagents and solvents were purchased from Sigma-Aldrich, Malingkrodt, Acros, Alfa, Tedia, or Fluka. $CH_2Cl_2$ fication. Thin layer chromatography (TLC) was performed with MERCK TLC silica gel 60 $F_{254}$ precoated plates. The starting materials and products were visualized with UV light (254 nm). Further confirmation was carried out by staining with 5% p-anisaldehyde, ninhydrin or ceric ammonium molybdate under heating. Flash chromatography was performed using Geduran Si 60 silica gel (230-400 mesh). Melting points were measured with MEL-TEMP and were uncorrected. NMR spectroscopy including $^1$H-NMR (500 MHz) and $^{13}$C-NMR (125 MHz, DEPT-135) was measured on Varian Unitylnova 500 MHz. D-solvents employed for NMR including $CD_3OD$, $CDCl_3$ and $C_6D_6$ were purchased from Cambridge Isotope Laboratories, Inc. Low-Resolution Mass Spectrometry (LRMS) was performed on an ESI-MS spectrometry employing VARIAN 901-MS Liquid Chromatography Tandem Mass Q-Tof Spectrometer. High Resolution Mass Spectrometry (HRMS) was performed using a varian HPLC (prostar series ESI/APCI) coupled mass detector of varian 901-MS (FT-ICR Mass) and triple quadrapole.

Commercial colorimetric COX (ovine) inhibitor screening assay kit was purchased from Cayman Chemical Ltd (760111). The assay kit contains both of COX-1 and COX-2 assay reagents. The specific activities of both of the two enzymes were equivalent according to the instructions by the suppliers. Commercial PTFE filter (0.45 μm) was purchased from Millipore.

[$^{123}$I]NaI was produced on a EBCO TR30 cyclotron (30 MeV) via the reaction $^{124}$Xe(p,2n), $^{123}$Cs decayed to $^{123}$Xe, and $^{123}$Xe decayed to $^{123}$I at Taiwan Nuclear Energy Research Initiative (NERI). All irradiations were carried out at a beam current of 120 μA, giving an average integrated current at the target of 300 μAh. After the injection of Gd-EOB-DTPA, the target was cooled for 6-8 hr for the $^{123}$Cs to decay to $^{123}$Xe and further transformation to $^{123}$I. The target was washed with firstly dilute NH$_4$OH (0.0016 N, 500 mL) followed by concentrated NH$_4$OH (0.16N, 4 mL) elution. The eluents were immediately loaded onto an alumina-B cartridge, which was pretreated with acetic acid (5.8 N, 10 mL). Before loading onto a second column of resin (AG50W-x8), NaOH (1N, 4 mL) was used for condition. The eluents were combined (2 to 3 mL) and a volume of ranging from 0.3 to 0.6 mL was used throughout the subsequent radiolabeling experiment. The radiolabeling was performed in a hood with sufficient ventilation and hepafilter for operation with $^{123}$I.

The compound of formula 1 was purified by a set of HPLC consisting of the components of a Waters 510 pump, a linear UVIS detector (254 nm) in series with a Berthhold γ-flow detector, on a ZORBAX SIL column (250 mm×9.4 mm, 5 μm) at 3 mL/min with MeOH/CHCl$_3$=1/99 as the mobile phase. Quality analysis of The compound of formula 1 was performed on the same HPLC setup as described above. The settings for radioactive ligand binding assay included a gel filtration column of TSKgel G3000PWx1 7.5×300 (mm) with a particle size of 10 μm which was purchased from Tosoh Bioscience LLC. The corresponding eluting conditions including PBS buffer and flow rate of 1 mL/min were employed throughout the experiment. The identity of The compound of formula 1 was confirmed with the compound of formula 2 on HPLC chromatogram after coinjection. The peak area of the UV absorbance at 254 nm that should correspond to the compound of formula 2 was calculated by interpolating to the standard curve relating mass to UV absorbance. Only a specific activity below 36 GBq/μmol can be measured accurately. Radioactive measurements were performed by a Capintec R15C dose calibrator.

All in vivo experiments were performed in compliance with the Taiwan National Health and Medical Research Council (NHMRC) Code of Practice for the care and use of animals for scientific purposes. Male-, Sprague-Dawley (SD) rats (49 weeks old) were obtained from the Animal Research Center (Chang-Gung Memorial Hospital, Taiwan). Rats were housed under constant environmental conditions and were allowed free access to food and water throughout the experimental period. In vivo studies were performed in a thioacetamide-induced cholangiocarcinoma (CCA) rat (37th week post administration) along with a normal rat as a control.

The rats were anaesthetized via inhalant isoflurane (Forthane, Abott) in 200 mL/min oxygen during the imaging study. SPECT system (X-SPECT/CT, Gamma Media, Northridge, Calif., USA) was used for small animal imaging study.

Example 1

4-(4'-iodobiphenyl-4-yl)-4-oxobutanoic acid (the Compound of Formula 4)

A mixture of succinic anhydride (893 mg, 9.0 mmol) and AlCl$_3$ (2.52 g, 18.8 mmol, 2.1 eq) in CH$_2$Cl$_2$ (45 mL) was stirred at room temperature for 20 min while the mixture became milky paste. The viscous mixture was moved to an ice bath and the stirring at dark was allowed for 2 min Upon the addition of the commercial 4-iodobiphenyl (2.5 g, 9.0 mmol), the mixture turned dark green. The stirring was allowed for 1 h. TLC (acetone:n-hexane=3:7) indicated the consumption of iodobiphenyl(R$_f$=0.87) and the formation of the compound of formula 4 (R$_f$=0.21). The mixture was poured into a mixture of HCl (12 N, 250 mL) in ice (500 g) and the stirring was allowed until the dark green color disappeared and yellow suspended solids were formed. After filtration of the mixtures using Büchner, the residual solid was collected. The mixture was dissolved in aqueous NaOH (1N, 250 mL). EtOAc was added for partition and the undesired organic impurities were removed. The aqueous layer was collected and HCl (12 N) was added to acidify the solution until the solids precipitated. The mixture was transferred to a Büchner followed by washing with distilled water to remove the rest acid. The residue was dried under reduced pressure and a fruity yellow solid (the compound of formula 4) was obtained in a crude yield of 89% (3.0 g).

The compound of formula 4 is identified by molecular weight, physical and chemical properties, spectroscopy, mass spectrometry and nuclear magnetic resonance spectroscopy respectively, as follows: Calcd. Cl$_6$H$_{13}$IO$_3$ [M]$^+$=379.99, ESI+Q-TOF MS, M=380.0 (m/z), [M+Na]$^+$=403.0, [2M+Na]=782.9; $^1$H-NMR (500 MHz, CD$_3$OD): δ 2.89 (t, J=6.5 Hz, 2H, aliphatic), 3.50-3.53 (m, 2H, aliphatic), 7.62-7.65 (m, 2H, Ar), 7.83-7.85 (m, 1H, Ar), 7.91-7.93 (m, 2H, Ar), 7.99 (d, J=7.5 Hz, 1H, Ar), 8.24 (d, J=8.0 Hz, 2H, Ar).

Example 2

4-(4'-iodobiphenyl-4-yl)-n-octyl-4-oxobutanamide (iodooctyl fenbufen amide; IOFA; the Compound of Formula 2)

To a two-necked round-bottomed flask containing a mixture of the compound of formula 4 in DMF (15 mL) was added HBTU (O-benzotriazol-1-yl-N,N,N',N',-tetramethyluronium hexafluorophospoate) (998 mg, 2.6 mmol) and diisopropyl ethylamine (680 mg, 0.9 mL, 5.2 mmol, 2 eq), sequentially. The stirring was allowed for 30 min. The commercial 1-amino octane (510 mg, 3.9 mmol, 1.5 eq) was added. The stirring was allowed for 15 min TLC (acetone/n-hexane=3:7) indicated the consumption of the compound of formula 4 (R$_f$=0.21) and the formation of the compound of formula 2 (R$_f$=0.56). The mixture was concentrated under high vacuo at 60° C. The residue was partitioned between aqueous HCl (1 N, 30 mL×2) and CHCl$_3$ (50 mL). The organic layers combined were concentrated under reduced pressure. The residue obtained was purified using flash chromatography with eluents of acetone/CHCl$_3$=1:29 to provide the compound of formula 2 (a pale yellow solid) with a plastic-like smelling in 73% yield (938 mg). The compound of formula 2 was fractionated by HPLC with eluents of MeOH/CHCl$_3$=1:99, t$_R$=17.3 min white solid, mp: 181-182° C.; Calcd. C$_{24}$H$_{30}$INO$_2$ [M]$^+$=491.1, ESI+Q-TOF MS, M=491.1 (m/z), [M+H]$^+$=492.1, [M+Na]$^+$=514.1; HRMS-ESI, Calcd. [M+H]$^+$=492.13995, [M+Na]$^+$=514.12189;

found: [M+H]$^+$=492.13955, [M+Na]$^+$=514.12173; $^1$H-NMR (500 MHz, CDCl$_3$): δ 0.87 (t, J=7.0 Hz, 3H, octyl, CH$_3$), 1.26-1.32 (m, 10H, octyl, CH$_2$), 1.50 (t, J=7.0 Hz, 2H, Octyl, CH$_2$), 2.62 (t, J=6.5 Hz, 2H, aliphatic, CH$_2$), 3.24 (q, J=7.0 Hz, 2H, octyl, CH$_2$), 3.39 (t, J=7.0 Hz, 2H, aliphatic, CH$_2$), 5.77 (bs, 1H, amide), 7.35 (d, J=8.5 Hz, 2H, Ar), 7.63 (d, J=8.0 Hz, 2H, Ar), 7.79 (d, J=8.5 Hz, 2H, Ar), 8.05 (d, J=8.5 Hz, 2H, Ar); $^{13}$C-NMR (125 MHz, CDCl$_3$): δ 14.07 (Octyl-CH$_3$), 22.62 (Octyl, CH$_2$), 26.88 (Octyl, CH$_2$), 29.18 (Octyl, CH$_2$), 29.23 (Octyl, CH$_2$), 29.59 (Octyl, CH$_2$), 30.37 (Octyl, CH$_2$), 31.76 (NH—CO—CH$_2$), 34.21 (Ar—CO—CH$_2$), 39.68 (CO—NH—CH$_2$), 94.28 (Ar, C—I), 127.00 (Ar, CH), 128.78 (Ar, CH), 129.00 (Ar, CH), 135.61 (Ar, C—CO), 138.06 (Ar, CH), 139.32 (Ar, C—Ar), 144.69 (C—Ar), 171.88 (NH—CO), 198.64 (Ar—CO).

Example 3

N-octyl-4-oxo-4-(4'-(trimethylstannyl)biphenyl-4-yl) butanamide (the Compound of Formula 3)

To a flask (10 mL) containg the compound of formula 2 (100 mg, 0.2 mmol) in 1,4-dioxane (1 mL) was added bis (triphenylphosphine)palladium dichloride (5 mg, 0.007 mmol, 0.03 eq) and hexamethylditin (237 mg, 0.15 mL, 0.72 mmol, 3.6 eq), sequentially. The mixture was warmed to 85° C. and the stirring was allowed for 15 min. TLC (acetone/CHCl$_3$=1:19) indicated the consumption of the compound of formula 2 (R$_f$=0.50) and the formation of the compound of formula 3 (R$_f$=0.55). The mixture was filtered through a celite pad and the filtrates were concentrated under reduced pressure. The residue obtained was purified using flash chromatography with eluents of EtOAc/n-hexane=2:8 to provide the compound of formula 3 (a white paste) in 56% yield (61 mg).

The compound of formula 3 was obtained through fractionation with HPLC using eluents of EtOAc/n-hexane=1:1, t$_R$=11.0 min. A smell of a combination of plastic and acid was notified. Calcd. C$_{27}$H$_{39}$NO$_2$Sn [M]$^+$=525.20 (41.5%), 527.20 (75.4%), 528.20 (44.8%), 529.20 (100.0%), ESI+Q-TOF MS, [M+H]$^+$=526.0 (29%), 528.1 (71%), 529.0 (43%), 530.1 (100%); HRMS-ESI, Calcd. [M+H]$^+$=530.20810, [M+Na]$^+$=552.19005; found: [M+H]$^+$=530.20767, [M+Na]$^+$=552.19021; $^1$H-NMR (500 MHz, C$_6$D$_6$): δ 0.25 (t, J=27.5 Hz, 9H, Sn—CH$_3$), 0.89 (t, J=7.5 Hz, 3H, aliphatic), 1.14-1.20 (m, 8H, aliphatic), 1.25-1.30 (m, 4H, aliphatic), 2.39 (t, J=6.5 Hz, 2H, aliphatic), 3.12-3.17 (m, 4H, aliphatic), 5.11 (bs, 1H, amide), 7.15-7.50 (m, 6H, Ar), 7.95 (d, J=8.5 Hz, 2H, Ar); $^{13}$C-NMR (125 MHz, CDCl$_3$): δ −9.55 (Sn—CH$_3$), 14.06 (Octyl-CH$_3$), 22.61 (Octyl, CH$_2$), 26.88 (Octyl, CH$_2$), 29.17 (Octyl, CH$_2$), 29.23 (Octyl, CH$_2$), 29.57 (Octyl, CH$_2$), 30.41 (Octyl, CH$_2$), 31.75 (NHCO—CH$_2$), 34.22 (NHCO—CH$_2$), 39.66 (CONH—CH$_2$), 126.70 (Ar, CH), 127.17 (Ar, CH), 128.66 (Ar, CH), 135.23 (Ar, C—CO), 136.40 (Ar, CH), 139.62 (Ar, C—Sn), 142.69 (Ar, C—Ar), 145.95 (Ar, C—Ar), 171.97 (CO—NH), 198.70 (Ar—CO).

Example 4

Preradiolabeling of the Organostannyl Compound of Formula 3 with Nonradioactive NaI A sample vial (50 mL) containing NaI (7.8 mg, 0.052 mmol, 7.5 eq) and double distilled water (0.5 mL) was sonicated for 2 min. A solution of glacial AcOH and 30% H$_2$O$_2$ (1:1.5 v/v) was added and the sonication was allowed for 1 min. After addition of the solution of the compound of formula 3 (4 mg, 0.007 mmol, 1 eq) in CH$_2$Cl$_2$ (2 mL), the compound of formula 3 was precursor which could react with nonradioactive Iodine ($^{127}$I) and radioactive Iodine ($^{123}$I). The mixture was sonicated for 20 min. The quenching reagent Na$_2$S$_2$O$_3$ (0.1 M, 10 mL) was added. The mixture was then partitioned by using additional H$_2$O (5 mL) and CH$_2$Cl$_2$ (10 mL). The organic layer was collected for subsequent loading onto a neutral alumina cartridge followed by washing with the solution of CH$_2$Cl$_2$ and MeOH (2:1, v/v, 10 mL). After concentration under reduced pressure, the residue was purified with HPLC (Si-100) using eluents of CH$_2$Cl$_2$:MeOH=99:1 to provide the desired fractionations: t$_R$=17.2 min for compound of formula 2; t$_R$=18 2 min for the destannylated byproduct OFA; see also the radiochemical labeling section. After concentration under reduced pressure, the desired compound of formula 2 was obtained in 50% yield (2 mg).

Example 5

Radioactive 4-(4'-[$^{123}$I]iodobiphenyl-4-yl)-N-octyl-4-oxobutanamide([$^{123}$I]IOFA; the Compound of Formula 1)

To a round-bottomed flask (25 mL) charging with a mixture of [$^{123}$I]NaI$_{(aq)}$ (75 mCi) in H$_2$O (less than 0.6 mL) was added glacial AcOH (3.5 mL) and H$_2$SO$_4$ (0.06 mL), sequentially. The stirring was allowed for 1 min. A mixed solution (3.5 mL) of glacial AcOH and aqueous H$_2$O$_2$ (30% wt) in a ratio of 2:3 (v/v) was added and the mixture was vigorously stirred for 1 min. A solution of the organostannyl compound 3 (9 mg) in CH$_2$Cl$_2$ (1 mL) was added. The vigorous stirring at rt was allowed for 20 min. The reaction was quenched by adding Na$_2$S$_2$O$_3$ (2 M, 0.8 mL). The mixture was then partitioned and the organic layer was collected. The residual aqueous layer was further back-extracted with CH$_2$Cl$_2$ (1 mL) twice. The organic layers combined were treated with 7 big spatulas of Na$_2$SO$_4$ followed by gravity filtration. The filtrates were loaded onto a CH$_2$Cl$_2$-preconditioned Alumnia N cartridge followed by washing with a mixed solution of CH$_2$Cl$_2$ and MeOH (3 mL, 2:1 v/v). The filtrates were concentrated under reduced pressure and the residue was further purified with HPLC using eluents of MeOH/CHCl$_3$=1:99, t$_R$=15.0 min (Radio). Fractions to the compound of formula 1 isolated from several injections were combined followed by concentration under reduced pressure to provide the compound of formula 1 in 15% radiochemical yield (8.1 mCi, decay corrected). Specific radioactivity and radiochemical purity were 36 GBq/μmole and 99%, respectively. Regarding animal SPECT imaging, the cholangiocarcinoma tumor-bearing rat and control rat were each injected with a dosage of 0.76 mCi/1 mL and 1.39 mCi/1 mL, respectively.

In present invention, the compound of formula 3 was formed by the compound of formula 2 via metal-halogen exchange, subsequently the compound of formula 1 was form by the compound of formula 3 via radiolabeling, it should have sufficient the compound of formula 2 to prepare the compound of formula 3. In FIG. 1, chromatogram for the compound of formula 1 (15.05 min) prior to HPLC purification. Normal phase column (Si-100) was employed. Red line: radioactivity, blue line: UV signal at 254 nm Example 6

Bioassay of Competitive Inhibition of the Substrate Transfer (CIST) by Cyclooxygenase (COX)

6.1 Nonradioactive Inhibition Assay

The procedure as stated by the product supplier was adopted through the whole assay. In brief, inhibitors were diluted with ethanol to the final working concentrations ranging either from $10^{-3}$ to $10^3$ μM for positive controls: SC560 and SC58125 or from $10^{-1}$ to $10^5$ μM for iodooctyl fenbufen amide (IOFA), fenbufen and uridine, respectively. The inhibition percentage was calculated as {1-[(absorption by substrate−absorption without enzyme)−(absorption by inhibitor−absorption without enzyme)/(absorption by substrate−absorption without enzyme)]}×100%.

Figure 2:
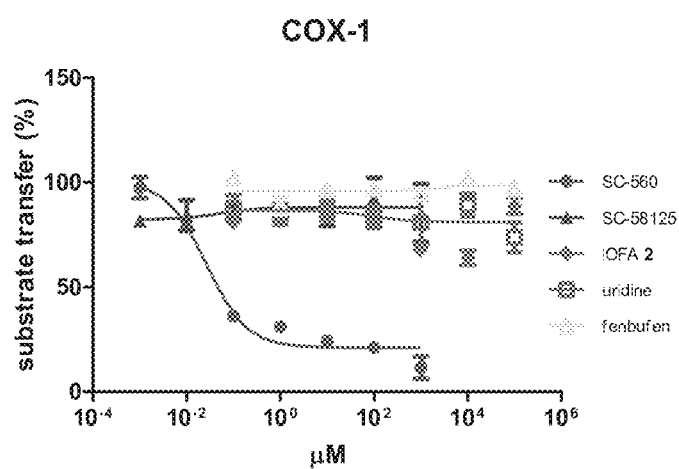
FIG. 2 shows the inhibition of the substrate transfer by COX-1 (A) and COX-2 (B) under the presence of tested compounds at various concentrations. Uridine is used as a negative control. Sc-560 and Sc-58125 were used as COX-1 and COX-2 specific inhibitors, respectively.
Figure 2B:
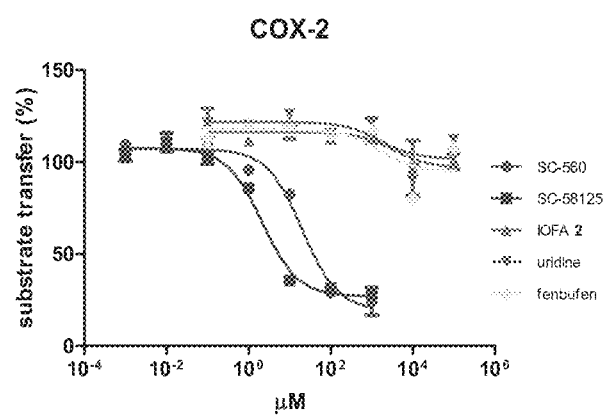

Both the COX-2 specific (SC-58125) and nonspecific (SC-560) inhibitors were used as the positive controls throughout the assay. The assay result shows that the compound of formula 2 displays marginal competitive inhibition against the reduction of the colorimetric substrate by COX-1 and COX-2. As shown in FIG. 2, inhibition of the substrate transfer by COX-1 (A) and COX-2 (B) under the presence of tested compounds (Table 1) at various concentrations. Uridine is used as a negative control. Sc-560 and Sc-58125 were used as COX-1 and COX-2 specific inhibitors, respectively.

TABLE 1

Comparison of the $IC_{50}$ values obtained from the present assay and the literature data.

| | $IC_{50}$ value | | | |
| --- | --- | --- | --- | --- |
| | COX-1 (μM) | | COX-2 (μM) | |
| Substrate | this assay | lit. data | this assay | lit. data |
| IOFA | >10 | N.A. | >10 | N.A. |
| Resveratrol | 3.9 | $1.56^{32}$ | 50 | $0.99^{33}$ |
| SC-58125 | >10 | $>10^{34}$ | 5 | $0.05^{34}$ |
| SC-560 | 0.060 | $0.009^{35}$ | 2.5 | $6.3^{35}$ |
| uridine | >10 | N.A. | >10 | N.A. |
| fenbufen | >10 | $3.9^{36}$ | >10 | $8.1^{36}$ |

6.2 Radioligand Binding Assay

The binding experiment was carried out in an eppendorf (0.2 mL) and stood for 10 min for equilibrium. An aliquot (10 μL) was drawn from the commercial stock solution (200 μL). Additional 30 μL of tris buffer (0.1 M, pH=8.0) was added. The solution (40 μL) of COX-1 or COX-2 each was added into a tris buffer (50 μL) together with the addition of a solution of the radiotracer the compound of formula 1 in EtOH with concentration ranging from 66 μCi/10 μL to 70 μCi/10 μL. The whole mixture (100 μL) was incubated at 25° C. for 15 min followed by submission to purification using HPLC. PBS buffer (0.1 M, pH=7.3) was employed as the eluent and the flow rate was set to be 1 mL/min.

The assay was based on that the retention time of the bound complex between radiolabeled ligand and enzyme was different from that of the unbound ligand in HPLC. Prior to the submission of the binding product mixtures to HPLC analysis, a minimal amount of enzyme (10 μL) from the commercial stock solution (200 μL) was introduced to assure the formation of the radioligand-enzyme complex for analysis. The pronounced nonpolarity of the radioligand of the compound of formula 1 might prevent from the use of polar eluents for HPLC chromatography. In our hands, water-based PBS buffer as the eluting solvent did not affect the retention time of the compound of formula 1.

Figure 3A:
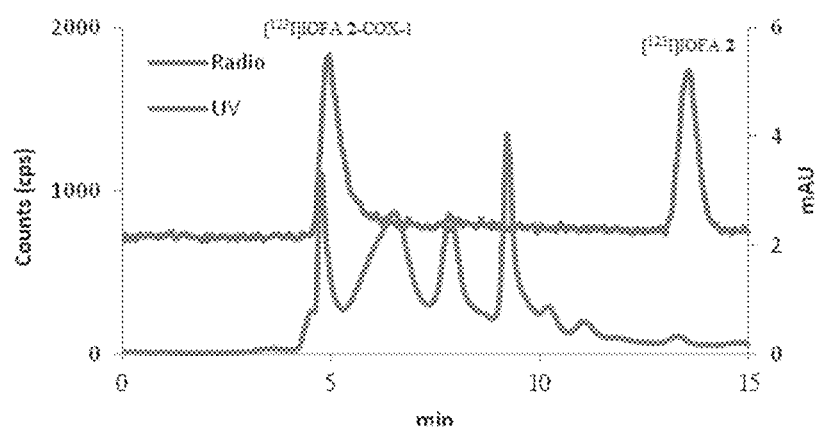
FIG. 3 is a HPLC chromatogram of the mixture generated from the binding experiments of the compound of formula 1 with (A) COX-1 and (B) COX-2.
Figure 3B:
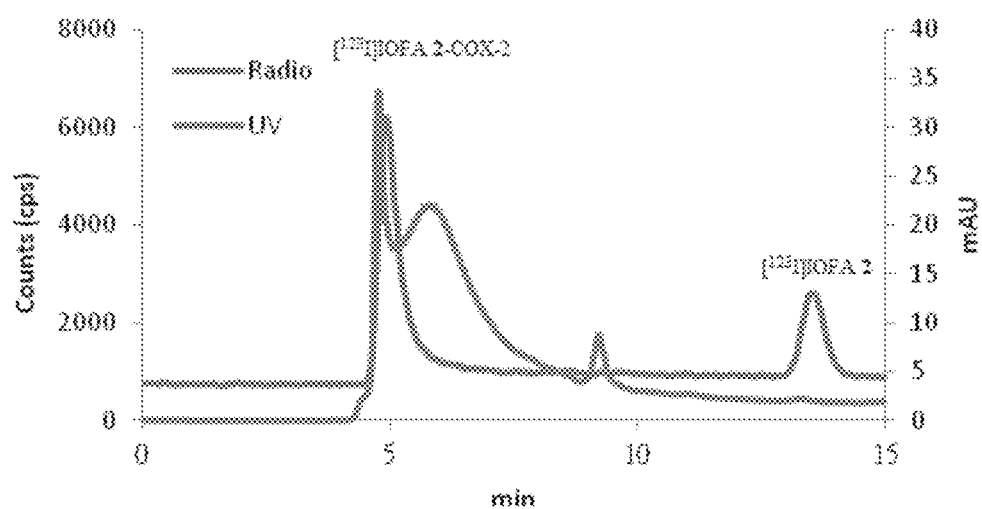

As shown in FIG. 3, HPLC chromatograms of the mixture generated from the binding experiments of the compound of formula 1 with (A) COX-1 and (B) COX-2. Binding yield=peak area at 5 min/(peak area at 5 min+peak area at 13.6 min) CPS: counts per second. (A) the compound of formula 1-COX-1 bound conjugate ($t_R$=5 0 min) and the residual unbound the compound of formula 1 ($t_R$=13.6 min) Binding yield=56%. Intact form the compound of formula 1 remained=44% (13.6 min) (B) the compound of formula 1-COX-2 bound conjugate ($t_R$=5.0 min) and the residual unbound the compound of formula 1 ($t_R$=13.6 min) Binding yield=79%. Intact form remained=21% (13.6 min).

Whereas the nonradioactive assay of CIST shows that the compound of formula 2 is neither a potent nor a selective COX inhibitor, the radioligand binding assay using HPLC, however, indicates its preferential selectivity toward COX-2 rather than COX-1 with an affinity ratio of 1.4:1 calculated from accumulated radioactivity fraction of 76% vs. 56%.

Example 7

Tumor Imaging Section

Figure 4:
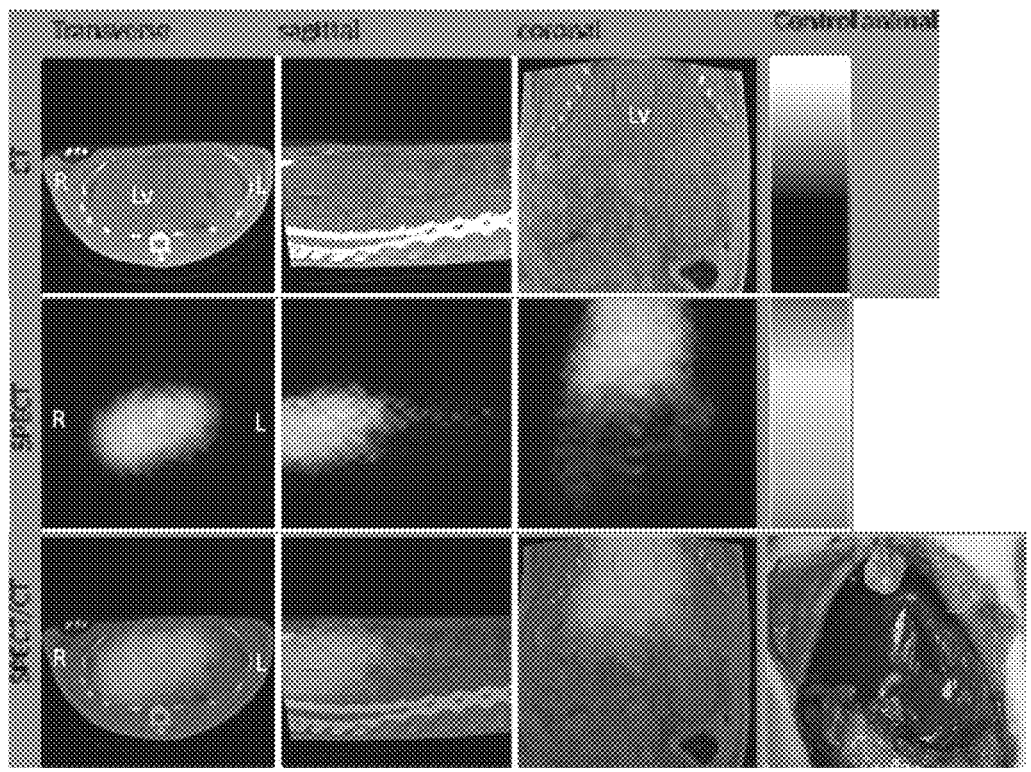
FIG. 4 (A) is a SPECT/CT image of the normal rat using the compound of formula 1 taken from 10 to 30 mins post injection. Injection dose: 1.39 mCi/1 mL. Lv: Liver.
Figure 4:
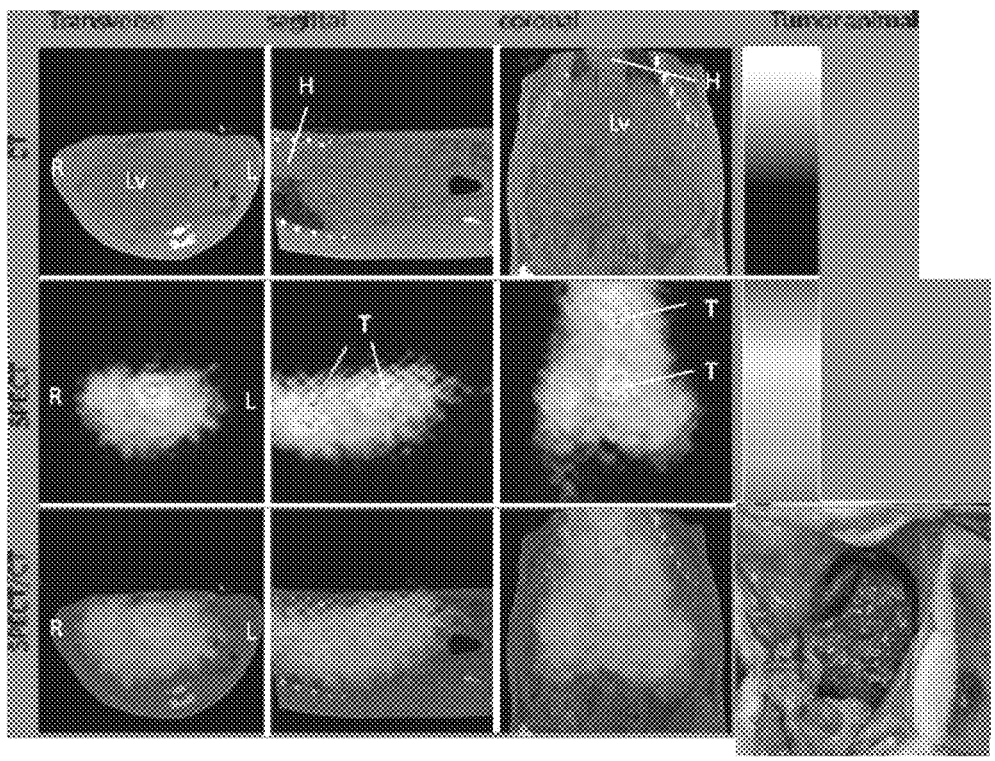

The compound of formula 1 (0.76 mCi/1 mL) was administered by the CCA rat via tail vein injection to obtain a summation of one-hour Single Photon Emission Computer Tomography (SPECT) imaging data (FIG. 4(A)). The normal rat was injected with the residual radioactivity of the compound of formula 1 (1.39 mCi/1 mL) (FIG. 4 (B)). All in vivo experiments were performed in compliance with the NHMRC Taiwan Code of Practice for the care and use of animals for scientific purposes, and the raw data from the image further analyzed by Preclinical Multi-Modality Data Analysis software (PMOD Technologies Ltd, Zurich, Switzerland).

Whereas the two injections were attempted by adjusting the volume of solvents so that equivalent specific activities could be achieved, the normal rat received an excess of specific activity. The in-vivo distribution of radioactivity in the normal rat showed a homogeneous pattern, which was localized mainly in the liver and partly in the heart 30 mins post administration (FIG. 4 (A)). By contrast, a heterogeneous radioactivity accumulation was addressed in the liver of CCA tumor rat. Specifically, those regions showing hot spots as indicated by the arrows are equivalent to the white matters of the photograph taken for the same rat after sacrifice (FIG. 4 (B), right lower corner). The white matters are indication of the tumor lesions according to the justification by clinician. The specimens of the liver of each of the two rats were further analyzed by histological stainings against COX-1 and COX-2. Clearly, the positive stainings of both COX-1 and COX-2 were solely found in the CCA tumor rat but not the normal rat. Hence, the inflammation is suggested to correlate with the tumor progression.

Figure 5:
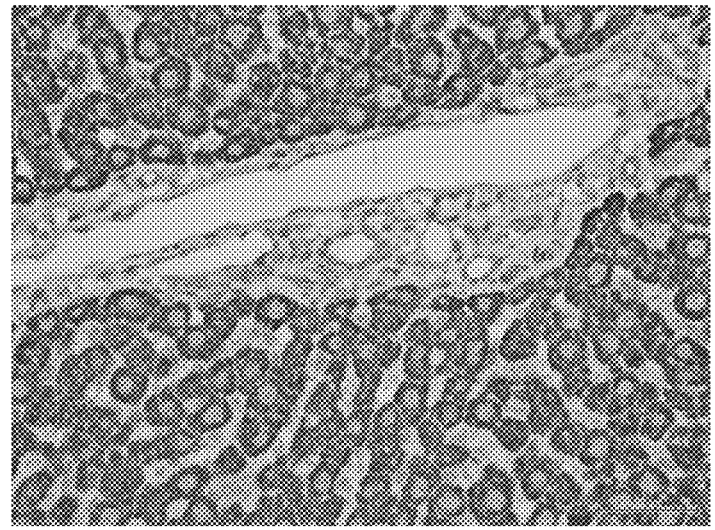
FIG. 5 is an immunostaining image: (A) Negative COX-1 immunoistaining of normal bile duct of the control rat (×400). (B) Positive cytoplasmic immunoistaing of COX-1 of the CCA rat (×400). (C) Negative COX-2 immunoistaining of normal bile duct of the control rat (×400). (D) Positive cytoplasmic immunoistaing of COX-2 of the CCA rat (×400).
Figure 5:
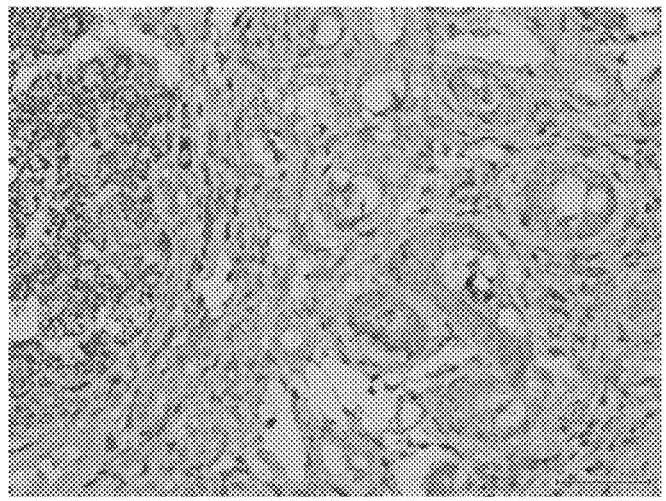
Figure 5:
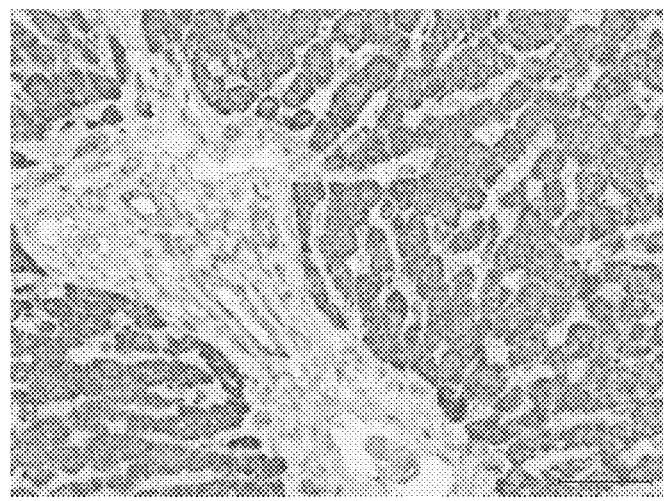
Figure 5:
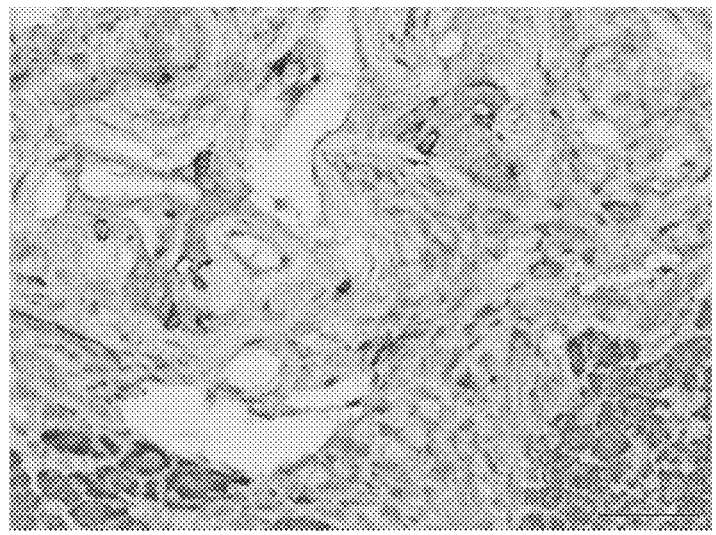

As shown in FIG. 4 (A), a SPECT/CT image of the normal rat using the compound of formula 1 were taken from 10 to 30 mins post injection. Injection dose: 1.39 mCi/1 mL. Lv: Liver; In FIG. 4 (B), a SPECT/CT images of CCA rat (feeding with TAA for 24 weeks) were taken from 10 to 30 mins post injection. Injection dose: 0.76 mCi/1 mL. Lv: liver, H: heart, T: tumor. The heterogeneous distribution of the radioactivity was indicative of the presence of tumors. The two red spots indicated the tumor lesions which were also observed from the photograph (right below corner) in respect of few white matters as shown by the arrows. As shown in FIG. 5. Immunostaining image: (A) Negative COX-1 immunoistaining of normal bile duct of the control rat (×400). (B) Positive cytoplasmic immunostaing of COX-1 of the CCA rat (×400). (C) Negative COX-2 immunoistaining of normal bile duct of the control rat (×400). (D) Positive cytoplasmic immunostaing of COX-2 of the CCA rat (×400).

In summary, the present invention provides a method of preparing the compound of formula 1 with a radiochemical yield of 15%, a specific activity of 37 GBq/μmol and radiochemical purity of 95%. Further investigation of the binding affinity of the compound of formula 1 toward COX-1 and COX-2 using HPLC in conjugation with a gel filtration column showed its preferable affinity toward COX-2 than COX-1. Whereas CIST assay of IOFA (iodooctyl fenbufen amide) showed a comparable marginal bioactivity as that of the parent fenbufen, the radioactive binding assay of the compound of formula 1 encouraged the subsequent in-vivo imaging. A potential binding site of COX might exist for this interaction which could not be assessed by the current CIST assay.

Results from both of the noninvasive SPECT imagings of the compound of formula 1 in the CCA tumor rat and the photographs after sacrifice have been correlated in respect of the hot spots and the white matters of tumor lesion. The expression levels of both COX of the liver of the CCA tumor rat were significantly higher than that of the control rat in terms of the immunohistological stainings. The marked tumor-associated accumulation of radioactivity of the compound of formula 1 clearly showed its imaging potential for tumor diagnosis. Based on the preferential binding affinity of the compound of formula 1 toward COX-2, it was hypothesized that the inflammation has be correlated to the tumor lesion in the liver of the CCA tumor rat.

Thus, the present invention provides a method of using the compound of formula 1 to estimate the distribution of cyclooxygenase. The present invention could be applied in single photon emission tomography (SPECT) image to estimate the tumorigenesis, metastasis and to detect early inflammatory lesion of a tumor by the distribution of cyclooxygenase by the positive correlation of inflammation to tumor lesion. And the compound of the present invention is a non steroid anti inflammatory drug, it has the advantages of simpler process, lower cost.

What is claimed is:

1. A method of detecting an early inflammatory lesion of a tumor comprising: administering a compound of formula 1 as a tracer of an image-forming system, and

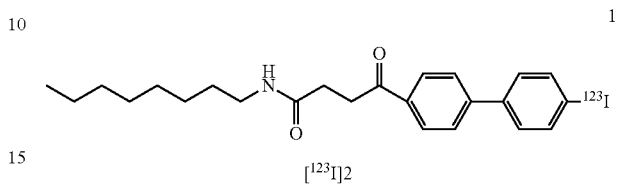

[$^{123}$I]2 detecting the binding affinity of the compound of formula 1 with cyclooxygenase to produce a signal, wherein the cyclooxygenase is cyclooxygenase-1 (COX-1) or cyclooxygenase-2 (COX-2), wherein the signal is a hot spot displayed by radioactive accumulation and the tumor is a liver tumor.

2. The method according to claim 1, wherein the image-forming system is a single photon emission tomography (SPECT).

3. The method according to claim 1, wherein the hot spot is positively correlated to the tumor lesion.

* * * * *